United States Patent [19]
Griffith

[11] Patent Number: 5,850,008
[45] Date of Patent: Dec. 15, 1998

[54] INBRED CORN LINE LH263

[75] Inventor: William D. Griffith, Greenwood, Ind.

[73] Assignee: Holden's Foundation Seeds, Inc., Williamsburg, Iowa

[21] Appl. No.: 761,672

[22] Filed: Dec. 6, 1996

[51] Int. Cl.$^6$ .............................. A01H 5/00; A01H 4/00; A01H 1/00; C12N 5/04
[52] U.S. Cl. .................. 800/200; 800/250; 800/DIG. 56; 47/58; 47/DIG. 1; 435/412; 435/424; 435/430; 435/430.1
[58] Field of Search ...................................... 800/200, 205, 800/250, DIG. 56; 47/58, DIG. 1; 435/172.3, 172.1, 412, 424, 430, 430.1

Primary Examiner—Gary Benzion
Attorney, Agent, or Firm—Rothwell, Figg, Ernst & Kurz, P.C.

[57] ABSTRACT

A novel inbred corn line, designated LH263, is disclosed. The invention relates to the seeds of inbred corn line LH263, to the plants of inbred corn line LH263 and to methods for producing a corn plant produced by crossing the inbred line LH263 with itself or another corn line. The invention further relates to hybrid corn seeds and plants produced by crossing the inbred line LH263 with another corn line.

11 Claims, No Drawings

INBRED CORN LINE LH263

BACKGROUND OF THE INVENTION

The present invention relates to a new and distinctive corn inbred line, designated LH263.

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size is important.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of corn breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research money to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (AxB and CxD) and then the two $F_1$ hybrids are crossed again (AXB) x (CxD). Much of the hybrid vigor exhibited by $F_1$ hybrids is lost in the next generation (F2). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of any individual with a specific genotype is less than 1 in 10,000. Thus, even if the entire genotype of the parents has been characterized and the desired genotype is known, only a few, if any, individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated LH263. This invention thus relates to the seeds of inbred corn line LH263, to the plants of inbred corn line LH263 and to methods for producing a corn plant produced by crossing the inbred line LH263 with itself or another corn line. This invention further relates to hybrid corn seeds and plants produced by crossing the inbred line LH263 with another corn line.

DEFINITIONS

In the description and tables which follow, a number of terms are used. In order to provide a clear and consistent understanding of the specification and claims, including the scope to be given such terms, the following definitions are provided:

Predicted RM. This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield in bushels/acre is the actual yield of the grain at harvest adjusted to 15.5% moisture.

Moisture. The moisture is the actual percentage moisture of the grain at harvest.

GDU Silk. The GDU silk (=heat unit silk) is the number of growing degree units (GDU) or heat units required for 50% of plants of an inbred line or hybrid to be in silk from the time of emergence.

GDU Pollen. The GDU pollen (=heat unit pollen) is the number of growing degree units (GDU) or heat units required for 50% of plants of an inbred line or hybrid to be in pollen from the time of emergence.

Growing degree units are calculated by the Barger Method, where the heat units for a 24-hour period are:

$$GDU = \frac{(\text{Max.} + \text{Min})}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging. This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging. The root lodging is the percentage of plants that root lodge; i.e., those that lean from the vertical axis at an approximate 30° angle or greater would be counted as root lodged.

Plant Height. This is a measure of the height of the hybrid from the ground to the tip of the tassel, and is measured in centimeters.

Ear Height. The ear height is a measure from the ground to the ear node attachment, and is measured in centimeters.

Dropped Ears. This is a measure of the number of dropped ears per plot, and represents the percentage of plants that dropped an ear prior to harvest.

DETAILED DESCRIPTION OF THE INVENTION

Inbred corn line LH263 is a yellow dent corn with superior characteristics, and provides an excellent parental line in crosses for producing first generation ($F_1$) hybrid corn. This inbred is best adapted for the Northcentral region of the United States.

Inbred corn line LH263 was developed from the cross LH51×LH211 by selfing and using the ear-row pedigree method of breeding. Yield, stalk quality, root quality, ear retention, disease tolerance, late plant greenness, late plant intactness, ear retention, pollen shedding ability, silking ability and corn borer tolerance were the criteria used to determine the rows from which ears were selected. Selfing and selection were practiced within the above $F_1$ cross for seven generations in the development of LH263. During the development of the line, crosses were made to inbred testers for the purpose of estimating the line's general and specific combining ability, and evaluations were run by the Williamsburg, Iowa Research Station. The inbred was evaluated further as a line and in numerous crosses by the Willaimsburg, Iowa Research Station and other research stations across the Corn Belt. The inbred has proven to have a very good combining ability in hybrid combinations and to produce hybrids which are better adapted for several environments within the Corn Belt.

The inbred has shown uniformity and stability for all traits, as described in the following variety description information. It has been self-pollinated and ear-rowed a sufficient number of generations, with careful attention to uniformity of plant type to ensure homozygosity and phenotypic stability. The line has been increased both by hand and sibbed in isolated fields with continued observation for uniformity. No variant traits have been observed or are expected in LH263.

Inbred corn line LH263, being substantially homozygous, can be reproduced by planting seeds of the line, growing the resultant corn plants under self-pollinating or sib-pollinating conditions with adequate isolation and harvesting the resultant seed, using techniques familiar to the agricultural arts.

Inbred corn line LH263 has the following morphologic and other characteristics (based primarily on data collected at Williamsburg, Iowa). The number in each parenthesis corresponds to the standard deviation in a sample size of 50, unless marked by an asterisk for which case the sample size is 15.

VARIETY DESCRIPTION INFORMATION

A. Maturity

INBRED=LH263

Developed In: Northcentral Region of Corn Belt

Heat Unit Silk: 1615.5 [93 days]

Heat Unit Pollen: 1558.5 [91 days]

$$\text{Heat Units:} = \frac{[\text{Max. Temp. } (\leq 82^\circ \text{ F.}) + \text{Min. Temp. } (\geq 50^\circ \text{ F.})]}{2} - 50$$

B. Plant Characteristics

Plant height (to tassel tip): 204.4 cm (6.3)

Ear height (to base of top ear): 84.3 cm (8.67)

Length of top ear internode: 15.8 cm (1.56)

Average Number of tillers: 0.0 (0)

Average Number of ears per stalk: 1.1 (0.0)

Anthocyanin of Brace Roots: Absent

C. Leaf

Width (widest point of ear node leaf): 8.5 cm (0.58)

Length (ear node leaf): 62.7 cm (3.27)

Number of leaves above top ear: 5 (0.44)

Leaf angle: 32° (6.74) (measured from 2nd leaf above ear at anthesis to stalk above leaf)

Color: medium green (Munsell code: 5GY 4/4)

Leaf sheath pubescence: 4 (rated on scale from 1=none to 9=like peach fuzz)

Marginal waves: 4 (rated on scale from 1=none to 9=many)

Longitudinal creases: 3 (rated on scale from 1=none to 9=many)

D. Tassel

Number of primary lateral branches: 8 (1.29)

Branch angle from central spike: 20° (8.20)

Tassel length (from top leaf collar to tassel tip): 45.3 cm (2.40)

Pollen shed: 7 (rated on scale from 0=male sterile to 9=heavy shed)

Anther color: yellow (Munsell code: 2.5GY 8/8)

Glume color: medium green (Munsell code: 5GY 5/6)

Bar glumes: Absent

E. Ear (Unhusked Data)

Silk color (3 days after emergence): light green (Munsell code: 2.5GY 8/8)

Fresh husk color (25 days after 50% silking): light green (Munsell code: 2.5GY 7/6)

Dry husk color (65 days after 50% silking): buff (Munsell code: 7.5YR 7/4)

Position of ear at dry husk stage: Pendent

Husk tightness: 5 (rated on scale from, 1=very loose to 9=very tight)

Husk extension: Medium (<8 cm)

F. Ear (Husked Data)

Length: 17.0 cm (1.73)

Diameter at midpoint: 36.8 mm (2.20)

Weight: 83.3 gm (19.78)

Number of kernel rows: 10 (0.70)

Kernel rows: Distinct

Row Alignment: straight

Shank length: 12.9 cm (3.34)

Taper of Ear: Average

G. Kernel (Dried)

Length: 10.3 mm (0.66)

Width: 9.5 mm (0.58)

Thickness: 4.0mm (0.0)

% Rounds (shape grade): 34.7 (5.16)*
Aleurone color pattern: Homozygous
Aleurone color: white
Hard endosperm color: yellow
Endosperm type: Normal starch
Gm Weight/100 seeds (unsized): 33.2 gm (0.45)*
H. Cob
Diameter at midpoint: 26.1 mm (1.70)
Color: Red (Munsell code: 10R 5/6)
I. Disease Resistance (rated from 1=most susceptible to 9=most resistant)
Northern leaf blight (*Exserohilum turcicum*) race 2: 8
Southern leaf blight (*Bipolaris maydis*) race 0: 8
*H. carbonum* race 3: 9
J. Agronomic Traits
Stay green (at 65 days after anthesis): 6 (rated on scale from 1=worst to 9=excellent)
% Dropped ears (at 65 days after anthesis): 0.0
% Pre-anthesis brittle snapping: 0.0
% Pre-anthesis root lodging: 0.0
% Post-anthesis root lodging (at 65 days after anthesis): 0.0

This invention is also directed to methods for producing a corn plant by crossing a first parent corn plant with a second parent corn plant, wherein the first or second corn plant is the inbred corn plant from the line LH263. Further, both first and second parent corn plants may be from the inbred line LH263. Therefore, any methods using the inbred corn line LH263 are part of this invention: selfing, backcrosses, hybrid breeding, and crosses to populations. Any plants produced using inbred corn line LH263 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as embryos, pollen, flowers, kernels, ears, cobs, leaves, husks, stalks, root, root tips, anthers, silk and the like.

Tissue culture of corn is described in U.S. Pat. Nos. 4,665,030, 4,806,483 and 4,843,005, incorporated herein by reference. Corn tissue culture procedures are also described in Green and Rhodes, "Plant Regeneration in Tissue Culture of Maize", *Maize for Biological Research* (Plant Molecular Biology Association, Charlottesville, Va. 1982), at 367–372. Thus, another aspect of this invention is to provide for cells which upon growth and differentiation produce the inbred line LH263.

Transformation of corn is described in U.S. Pat. Nos. 5,384,253, 5,489,520, 5,538,877 and 5,550,318, incorporated herein by reference. Corn transformation is also described in Prioli and Söndahl, "Plant Regeneration and Recovery of Fertile Plants from Protoplasts of Maize (*Zea Mays* L.)", *Bio/technology* 7:589–594 (1989); Shillito et al., "Regeneration of Fertile Plants from Protoplasts of Elite Inbred Maize", *Bio/technology* 7:581–587 (1989). Thus, another aspect of this invention is to provide inbred line LH263 which contains a heterologous gene.

LH263 is most similar to parental line LH211. However the most distinguishing difference is the number of kernel rows per ear. The number of kernel rows per ear of LH263 is less than the number of kernel rows per ear of LH211. The data for kernel rows per ear for LH263 and LH211 with 50 observations from two different planting dates during the 1996 growing season are as follows:

A) Average: LH263: 10.000 Standard Deviation: LH263: 0.904
LH211: 12.760 LH211: 0.981
Statistic: T=−14.64 (DF=97) Probability Value: 0.000
B) Average: LH263: 9.920 Standard Deviation: LH263: 0.695
LH211: 12.360 LH211: 1.12
Statistic: T=−13.08 (DF=81) Probability Value: 0.000

In both cases, the data suggests a significant difference at the 1% probability level according to a paired T-test. The means show that on average LH263 has less kernel rows per ear than LH211.

LH263 is a medium late season field corn inbred line that flowers one to two says earlier than LH51. It is a very good pollinator, but is not suitable for use as a seed parent. LH263 hybrids are higher yielding and average aproximately 1.5% less harvest moisture than comparable LH51 hybrids. The ears of LH263 hybrids are attractive due to their consistent, large size and moderately high placement on the stalk. LH263 hybrids display a robust appearance early in the season, while later in the growing season staygreen is only average. Corn borer removal of plant tops is most severe in LH263 crosses than comparable LH51 crosses. Lighter grain test weight may be of concern for some LH263 hybrids. Root strength of LH263 hybrids is excellent. LH263 hybrids are slightly higher yielding and 1–2% lower in harvest moisture than their LH51 and LH216 counterparts. LH263 hybrids have a long ear style.

TABLES

In the tables that follow, the traits and characteristics of inbred corn line LH263 are given in hybrid combination. The data collected on inbred corn line LH263 is presented for the key characteristics and traits. The tables present yield test information about LH263. LH263 was tested in several hybrid combinations at eight locations, with two or three replications per location. Information about these hybrids, as compared to several check hybrids, is presented.

The first pedigree listed in the comparison group is the hybrid containing LH263. Information for the pedigree includes:

1. Mean yield of the hybrid across all locations.
2. A mean for the percentage moisture (% M) for the hybrid across all locations.
3. A mean of the yield divided by the percentage moisture (Y/M) for the hybrid across all locations.
4. A mean of the percentage of plants with stalk lodging (% SL) across all locations.
5. A mean of the percentage of plants with root lodging (% RL) across all locations.
6. A mean of the percentage of plants with dropped ears (% DE).
7. The number of locations indicates the locations where these hybrids were tested together.

The series of hybrids listed under the hybrid containing LH263 are considered check hybrids. The check hybrids are compared to hybrids containing the inbred LH263.

The (+) or (−) sign in front of each number in each of the columns indicates how the mean values across plots of the hybrid containing inbred LH263 compare to the check crosses. A (+) or (−) sign in front of the number indicates that the mean of the hybrid containing inbred LH263 was greater or lesser, respectively, than the mean of the check hybrid. For example, a +4 in yield signifies that the hybrid containing inbred LH263 produced 4 bushels more corn than the check hybrid. If the value of the stalks has a (−) in front of the number 2, for example, then the hybrid containing the inbred LH263 had 2% less stalk lodging than the check hybrid.

Initial disease ratings of several inred lines were taken at Williamsburg, Iowa in 1995 and are as follows in which 0=excellent and 9=poor.

| Disease | LH263 | LH51 | LH59 | LH168 | LH172 | LH212 |
|---|---|---|---|---|---|---|
| Carbonum | 0.0 | 0.2 | 0.5 | 1.0 | 0.4 | 1.3 |
| Northern (race2) | 1.0 | 1.1 | 1.6 | 3.8 | 4.0 | 2.3 |
| Soutern | 1.0 | 1.1 | 1.5 | 4.3 | 3.5 | 1.7 |

DEPOSIT INFORMATION

Inbred seeds of LH263 have been placed on deposit with the American Type Culture Collection (ATCC), Rockville,

TABLE 1

Overall Comparisons of LH195 × LH263 Hybrids Vs. Check Hybrids

| Hybrid | Mean Yield | % M | Y/M | % SL | % RL | % DE | Plnt Hgt | Ear Hgt |
|---|---|---|---|---|---|---|---|---|
| LH195 × LH263 (at 12 Loc's, 1995) as Compared to: | 179 | 18.68 | 9.59 | 3 | 0 | 0 | 104 | 48 |
| LH195 × LH216 | +4 | −2.02 | +1.12 | 0 | 0 | 0 | −5 | 0 |
| LH200 × LH216 | −2 | −1.09 | +.43 | +1 | −1 | 0 | −5 | −1 |
| LH197 × LH51 | −5 | −.09 | −.20 | 0 | −1 | 0 | −3 | −2 |
| LH195 × LH212 | +3 | +.76 | −.22 | −2 | −2 | −1 | −6 | 0 |
| LH195 × LH59 | +14 | +1.22 | +.15 | −2 | −2 | −1 | −1 | 0 |

TABLE 2

Overall Comparisons of LH231 × LH263 Hybrids Vs. Check Hybrids

| Hybrid | Mean Yield | % M | Y/M | % SL | % RL | % DE | Plnt Hgt | Ear Hgt |
|---|---|---|---|---|---|---|---|---|
| LH231 × LH263 (at 10 Loc's, 1995) as compared to: | 165 | 17.07 | 9.66 | 4 | 1 | 0 | 107 | 41 |
| LH231 × LH51 | +6 | −1.55 | +1.11 | −1 | 0 | 0 | 0 | −4 |
| LH231 × LH185 | −10 | −.88 | −.06 | −2 | 0 | 0 | +1 | +3 |
| LH197 × LH59 | +7 | +.16 | +.29 | −2 | 0 | −1 | −2 | 0 |
| LH198 × LH185 | +7 | +.63 | +.05 | −2 | 0 | 0 | −4 | −2 |
| LH195 × LH59 | +1 | +.66 | −.36 | −1 | 0 | 0 | +16 | −2 |
| LH200 × LH59 | +2 | +.84 | −.34 | −3 | −2 | 0 | −2 | −3 |

TABLE 3

Overall comparisons of LH200 LH263 Hybrids Vs. Check Hybrids

| Hybrid | Mean Yield | % M | Y/M | % SL | % RL | % DE | Plnt Hgt | Ear Hgt |
|---|---|---|---|---|---|---|---|---|
| LH200 × LH263 (at 9 Loc's, 1995) as compared to: | 173 | 17.64 | 9.80 | 4 | 1 | 0 | 112 | 50 |
| LH200 × LH216 | +3 | −2.00 | +1.14 | +2 | −1 | −1 | −2 | +1 |
| LH231 × LH185 | +4 | +.31 | +.08 | −2 | −1 | 0 | +3 | +10 |
| LH200 × LH212 | +3 | +1.05 | −.45 | −2 | 0 | −1 | −3 | +4 |
| LH198 × LH185 | +2 | +1.13 | −.54 | +1 | −1 | 0 | +2 | +8 |
| LH195 × LH186 | +11 | +1.47 | −.23 | 0 | +1 | 0 | 0 | +6 |
| LH200 × LH186 | +13 | +1.77 | −.29 | −1 | +1 | −1 | 0 | +7 |
| LH235 × LH186 | +10 | +2.13 | −.67 | 0 | +1 | −1 | −6 | +2 |
| LH198 × LH186 | +16 | +2.25 | −.37 | 0 | 0 | −1 | −2 | +3 |

Md. 20852, under Deposit Accession Number 97819 on 6 Dec., 1996. The deposit of inbred LH263 consists of 2500 seeds. A Plant Variety Protection Certificate is being applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred corn seed designated LH263, having ATCC accession No. 97819.
2. A corn plant produced by growing the seed of claim 1.
3. Pollen of the plant of claim 2.
4. An ovule of the plant of claim 2.
5. An inbred corn plant having all the physiological and morphological characteristics of the inbred corn plant of claim 2.
6. A corn plant regenerated from a tissue culture of tissue obtained from the corn plant of claim 2, said regenerated corn plant having capable of expressing all the physiological and morphological characteristics of said corn plant of claim 2.
7. A method for producing first generation ($F_1$) hybrid corn seed comprising crossing a first inbred parent corn plant with a second inbred parent corn plant and harvesting the resultant first generation ($F_1$) seed, wherein one but not both of said first inbred parent corn plant and said second inbred parent corn plant is the corn plant of claim 2.
8. The method of claim 7 wherein said corn plant is the female parent.
9. The method of claim 7 wherein said corn plant is the male parent.
10. Hybrid seed produced by crossing a first inbred parent corn plant with a second inbred parent corn plant and harvesting the resultant hybrid seed, wherein one but not both of said first inbred parent corn plant and said second inbred parent corn plant is the corn plant of claim 2.
11. Hybrid corn plants grown from the hybrid seed of claim 10.

* * * * *